United States Patent [19]

Herzlinger et al.

[11] 3,985,123

[45] Oct. 12, 1976

[54] METHOD AND MEANS FOR MONITORING CARDIAC OUTPUT

[75] Inventors: George A. Herzlinger, Belmont; Armando Federico, Needham; Arthur R. Kantrowitz, Cambridge, all of Mass.

[73] Assignee: Avco Everett Research Laboratory, Inc., Everett, Mass.

[22] Filed: July 17, 1975

[21] Appl. No.: 596,907

[52] U.S. Cl. .......................... 128/2.05 F; 128/1 D; 128/2.05 V; 128/2.05 T
[51] Int. Cl.² .......................................... A61B 5/02
[58] Field of Search .......... 128/1 D, 2.05 D, 2.05 F, 128/2.05 R, 2.05 V, 2.05 T; 3/1.7, 1.2

[56] References Cited
UNITED STATES PATENTS

| | | | |
|---|---|---|---|
| 3,457,909 | 7/1969 | Laird | 128/1 D |
| 3,720,199 | 3/1973 | Rishton et al. | 128/1 D |
| 3,814,082 | 6/1974 | Taylor | 128/2.05 R |
| 3,831,590 | 8/1974 | Boyle et al. | 128/2.05 R |

OTHER PUBLICATIONS

I.E.E.E. Trans. on Bio–Med Engng. vol. BME–18, No. 1, (Jan. 1971), pp. 60–65.

Jacobs, R. R. et al., "A Pressure–Flow Catheter", Journ. of Assoc. for Advance. of Med. Instrn., vol. 6, No. 2, Mar.–Apr. 1972, p. 171.

Primary Examiner—Kyle L. Howell
Attorney, Agent, or Firm—Charles M. Hogan; Melvin E. Frederick

[57] ABSTRACT

A cardiac output monitor. The monitor receives signals representing radial arterial pressure, balloon pressure, balloon drive and balloon volume from an intraaortic balloon pumping system. These signals are processed to define balloon depletion pressure ($P_1$), ventricle ejection pressure ($P_2$), balloon volume (BV) and heart rate (HR). The monitor displays the cardiac output according to Cardiac output = $(P_2/P_1)$ (BV) (HR)

The monitor also indicates certain improper pumping system operations and can provide a continuous display.

23 Claims, 22 Drawing Figures

BALLOON DRIVE

BALLOON PUMP PRESSURE

RADIAL ARTERY PRESSURE

TIME

```
50  READY: ST= INPUT(0);
51  IF SHL(ST,7)=0 THEN
       GO TO READY;

52  OUTPUT(0)=0;
53  I=1; L=499;

54  A: CALL TIME (70);

55  JBTEST= INPUT(2);
56  JBTEST= JBTEST-
       SHL(SHR(JBTEST,1),1);

57  I=I+1;
58  IF I>150 THEN GO TO OFF;

59  IF JBTEST = 0 THEN GO TO A;

60  DO WHILE JBTEST=1;

61  IF I>200 THEN GO TO OFF;

62  CALL TIME (70);

63  JBTEST= INPUT(2);
64  JBTEST= JBTEST-
       SHL(SHR(JBTEST,1),1);
65  I=I+1;
66  END;
```

```
67  OUTPUT(2)=0;
68  CALL TIME (10);
69  OUTPUT(5)=0;
70  CALL TIME(10);
71  BP=INPUT(1);
72  OUTPUT(1)=0;
73  CALL TIME(10);

74  DO I = 0 TO L;
75  JB(I) = INPUT(2);
76  OUTPUT (5)=01011011B;
77  CALL TIME (64);
78  JP(I) = INPUT(1);
79  END;
```

80 KP, IPL=0;
81 IHF1=NEXTBP(0,.JB,L,.IL);
82 IF IHF1=0 THEN GO TO OFF;
83 BIGLOOP:IHF2=NEXT BP
   (IL,.JB,L,.IL);

84 IF IHF2=0
   THEN GO TO TIMEND;

85 KP=KP+1;
86 CALL MX (IHF1,SHR
   (IHF2+IHF1+IHF1+IHF1,2)
   +5,·JP,·IP MAX,·JP MAX,
   1);

87 CALL MN (IP MAX,IHF2,
   JP,·IP MIN;JP MIN, 1);

88 I=IPMAX;
89 K=SHR (JP MAX-JP MIN ,3);

63. DEFINE ONE HEART BEAT INTERVAL AND INCREMENT A HEART BEAT NUMBER IN THE MEMORY 34 AT A KP LOCATION 303

64. HAVE ALL THE SAMPLED INTERVALS BEEN PROCESSED ?

65. LOCATE THE MAXIMUM VALUE OF THE ARTERIAL PRESSURE SIGNAL AND STORE THE LOCATION (i.e., POINT H IN FIGURE 3) AND THE VALUE OF THE MAXIMUM, IN IPMAX AND JPMAX LOCATIONS 304 AND 305 IN THE MEMORY 34

66. LOCATE THE MINIMUM VALUE OF THE ARTERIAL PRESSURE SIGNAL AND STORE THE LOCATION (i.e., POINT L IN FIGURE 3) AND THE VALUE OF THE MINIMUM, IN IPMIN AND JPMIN LOCATIONS 306 AND 307 IN THE MEMORY 34

67. LOCATE THE POINT AT WHICH THE ARTERIAL PRESSURE HAS DROPPED 1/8 OF THE WAY FROM MAXIMUM TO MINIMUM (i.e., POINT I IN FIGURE 3)

```
90  B:I=I+1;
91  IF I>IP MAX +20 THEN GO
    TO TROUBLE;
92  IF JP(I)>JP MAX-K THEN
    GO TO B;
93  I45=I; IDPM=IP MIN-1;
94  IF IDPM<I 45 THEN GO TO
    TROUBLE;
95  DO I=I 45 TO IDPM;
96  IDP=I-I 45;
97  IPI= I+1; IMI=I-1;
98  JDP(IDP)=JP(IMI)-JP(IPI)+128;
99  END;
100 IDPM=IDPM-I45-2;
101 IF IDPM<5 THEN GO TO
    TROUBLE;
102 DO I=2 TO IDPM BY 2;
103 IMI=I-2; IPI=I+2;
104 JDDP(SHR(I,1))=JDP
    (IPI)-JDP(IMI)+128; END;
105 IDPM=SHR(IDPM,1);

106 CALL MX(1,IDPM,JDDP,I2DMX,
    .J 2DMX, 1);
107 CALL MN(1,I2DMX,JDDP,I2DMN,
    .J 2DMN, 1);
108 I 2DMX=SHL(I 2DMX,1);
109 I 2DMN=SHL(I 2DMN,1);
110 IPL=IPL+I 2DMX-I 2DMN;
111 IP=I 2DMN+I45;

112 IF JP(IP)-JP MIN<K+1
    THEN GO TO TROUBLE;
113 IF JP(IP)-JP(I 2DMX+
    I45)>SHR(JP MAX-
    JP MIN.,1)-4 THEN GO
    TO TROUBLE;

114 CALL MN(I 2DMN,I 2DMX,
    .JDP.IDPMN,JDPMN,2);
115 JPMX2= JP MIN;
```

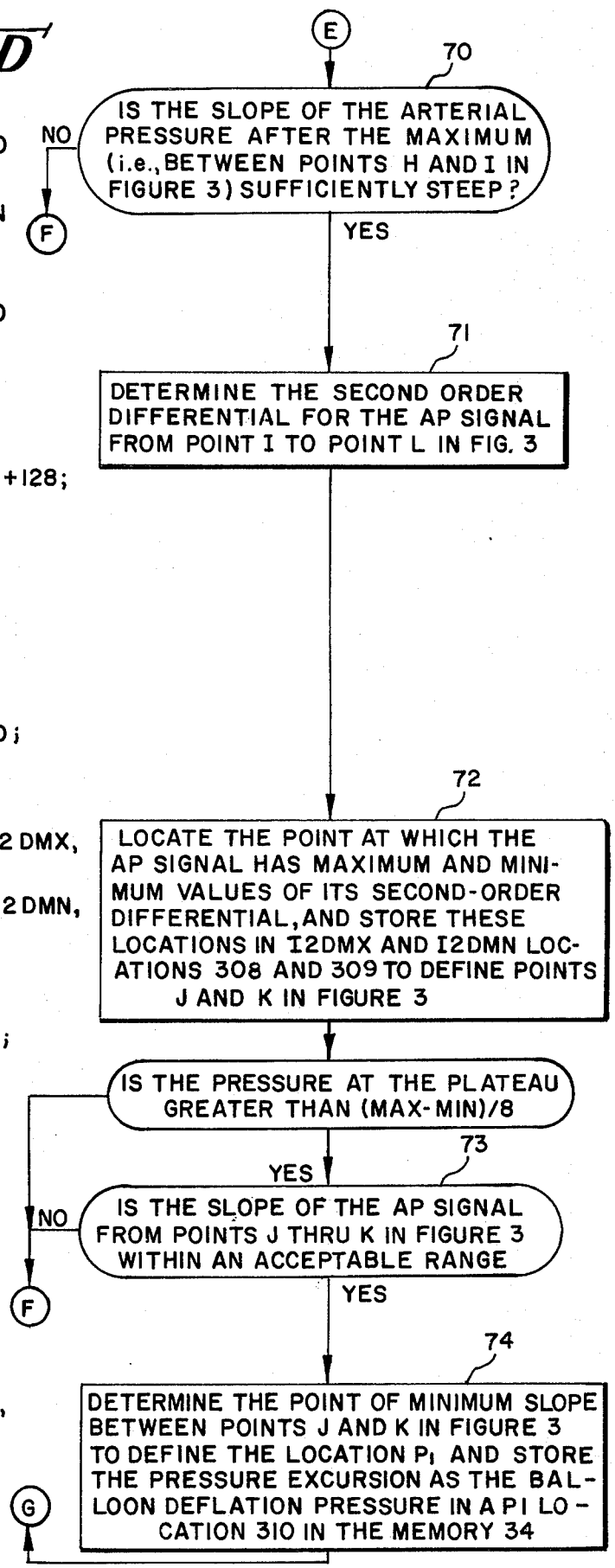

116 I=IP MIN ;
117 K=(JP MAX.+5*JP MIN )/6;
118 C:I=I+1;
119 IF I>IHF2-5 THEN GO TO TROUBLE;
120 IF JP(I)<K THEN GO TO C;

121 K=0; DO WHILE K<4;
122 I=I+1;
123 IF I>IHF2 THEN GO TO TROUBLE;
124 IF JPMX2>JP(I) THEN K=K+1;
125 ELSE DO ; IPMX2=I; JPMX2= JP(I); END;
126 END;
127 IF KP=1 THEN IPX21 = IPMX2;
128 JPMX2=JPMX2-JP MIN ;

129 JKR(KP)=(JPMX2*250 +125)/ (JP(IDPMN+I45)-JPMIN);

130 IHF1=IHF2;
131 GO TO BIGLOOP;

132 TIMEND: IF KP<2 THEN GO TO TROUBLE ;

133 JRA=0;
134 DO I=1 TO KP;
135 JRA=JRA+JKR(I);
136 END;
137 JRA=SHL(JRA,2)/KP;

138 IF JRA>1500 THEN
    JRA=(JRA-1500)*9/10+1500;

139 JHR=5*(IPMX2-IPX21)/(KP-1);
140 JHR=60000/JHR;

141 IPL=(IPL+SHR(KP,1))/KP
    *JHR/200;

142 IF IPL>12 THEN OUTPUT
    (3)=01010111B;

143 JC01=SHR(JRA,7);
144 JC02=(JRA-SHL(JC01,7))*JHR;
145 JC01=JC01*JHR+SHR
    (JC02,7);

146 JBV=0;
147 JBV=SHR(INPUT(3),5);
148 IF JBV=001B THEN JBV=46;
149 IF JBV=010B THEN JBV=63;
150 IF JBV=100B THEN JBV=80;

```
151 IDPM = SHR(JCO1,7);
152 JCO2=(JCO1-SHL(IDPM,7))×JBV;
153 JCO1= IDPM*JBV+SHR
    (JCO2,7);

154 IF JCO1 > 3000 THEN
    GO TO TROUBLE;

155 JCO1=JCO1*9/22+1;
156 DO CASE (BP+74)/75;
157 JCO1=JCO1;
158 JCO1=(75-BP)*22/
    JBV*JCO1/100+JCO1;
159 JCO1=JCO1-(BP-75)*22/
    JBV*JCO1/100;
160 GO TO TROUBLE;
161 END;
162 OUTPUT(7)=JCO1/100;
163 JCO2= JCO1-(JCO1/100)*100;
164 OUTPUT(6)=SHL(JCO2/10,4)+
    JCO2-(JCO2/10)*10;
165 GO TO FIN;

166 OFF: OUTPUT(6)=0;
167 OUTPUT(7)=0;
168 GO TO FIN;

169 TROUBLE: OUTPUT(4)=0;

170 FIN: GO TO READY;
171 HALT;
172 EOF;
```

```
1   MN: PROCEDURE (M,N,JTA,IMINA,JMINA,IGRD);
2   DECLARE (JTA,I,M,N,IMINA,JMINA);
3   (IGRD, JT BASED JTA, JMIN BASED JMINA) BY TE;
4   JMIN = JT(M);
5   IMIN = M;
6   DO I=M TO N BY IGRD;
7   IF JMIN>= JT(I) THEN DO;
8   JMIN=JT(I); IMIN=I;
9   END; END;
10  RETURN;
11  END MN;

12  MX: PROCEDURE (M,N,JTA,IMAXA,JMAXA,IGRD);
13  DECLARE (JTA,M,N,IMAXA, IMAX BASED IMAXA,I,JMAXA) ADDRESS;
14  DECLARE (IGRD,JT BASED JTA,JMAX BASED JMAXA) BYTE;
15  JMAX = JT(M);
16  IMAX = M;
17  DO I=M TO N BY IGRD;
18  IF JMAX<JT(I) THEN DO;
19  JMAX= JT(I); IMAX=I;
20  END; END;
21  RETURN;
22  END MX;

23  NEXTBP: PROCEDURE (IST, JBA,L,ILA) ADDRESS;
24  DECLARE (IST,JBA,L,I,II,ILA) ADDRESS, JB BASED JBA BY TE;
25  DECLARE IL BASED ILA ADDRESS;
26  I= IST+10;
27  IF JB(I)-SHL(SHR(JB(I),1),1)=1 THEN RETURN 0;
28  DO WHILE JB(I)=SHL(SHR(JB(I),1),1);
29  I=I+1; IF I>L-20 THEN RETURN 0;
30  END;
31  II=I;
32  DO WHILE JB(I)>SHL(SHR(JB(I),1),1);
33  I=I+1;
34  IF I>L THEN RETURN 0;
35  END;
36  IL=I;
37  RETURN SHR(II+IL,1);
38  END NEXTBP;

39  DECLARE JP(500) BY TE, I ADDRESS, L ADDRESS;
40  DECLARE (IHF1,IHF2,IL, IPMAX,IPMIN,I45,IDPM,I2DMX,I2DMN,IPX21,
    IPMX2,
41  IP, JRA, JCO1, JCO2, JHR) ADDRESS, JKR(10) ADDRESS;
```

Fig. 5H

```
42  DECLARE JDP(80) BY TE, JDDP(40) BY TE,(BIGLOOP,TIMEND,TROUBLE,
    OFF, FIN) LABEL;
43  (B,C,) LABEL;
44  DECLARE (IMI,IPI) ADDRESS;
45  DECLARE (JBTEST, BP) BY TE, A LABEL;
46  DECLARE (K,KP,IPL,JPMAX,JPMIN,JBV,IDPMN,IDP,J2DMX,J2DMN,JPMX2)
    BY TE;
47  DECLARE ST BY TE, READY LABEL;
48  DECLARE JDPMN BY TE, DMY(240) BYTE;
49  DECLARE JB(512) BYTE;
```

Fig. 5I

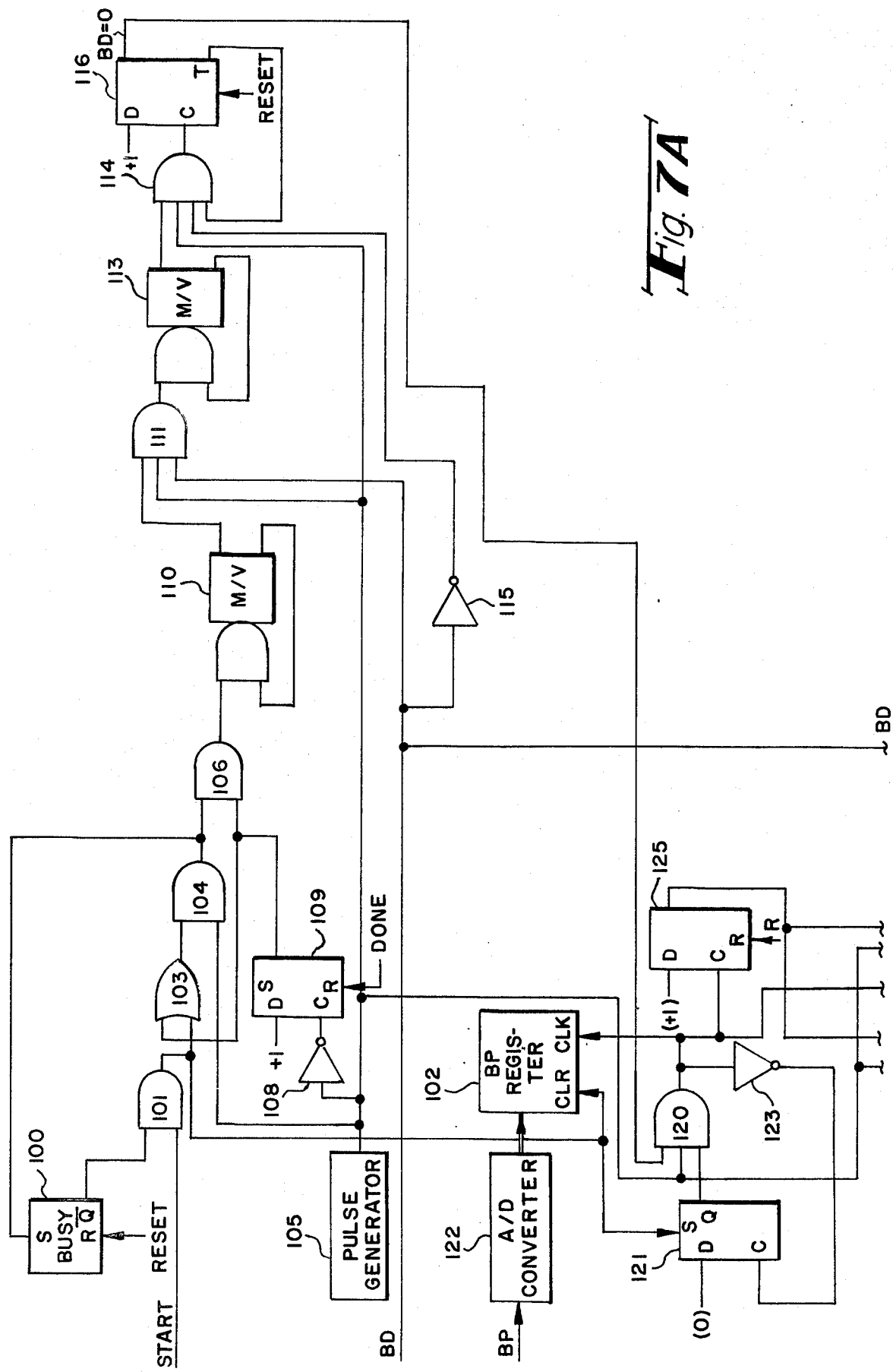

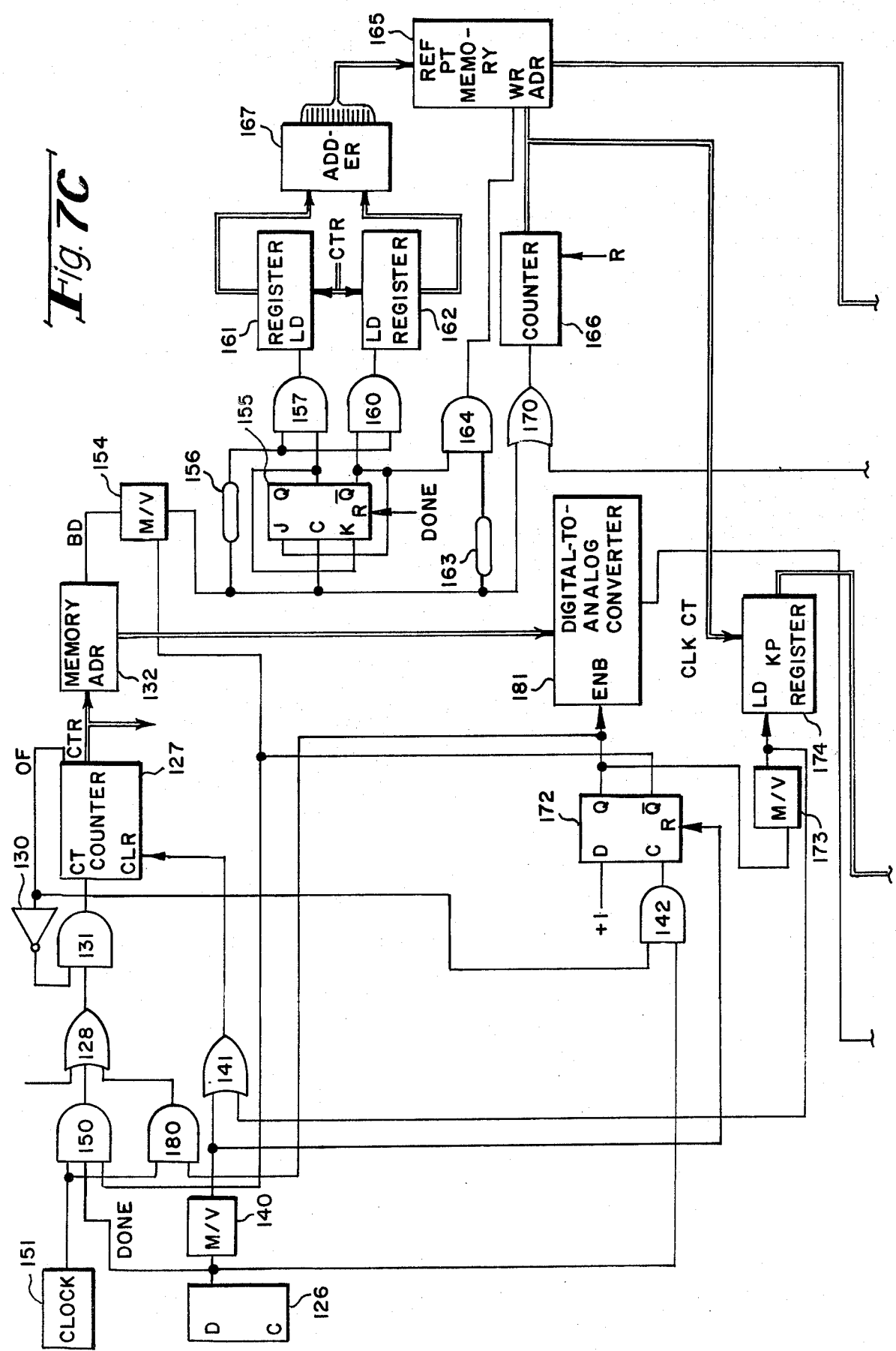

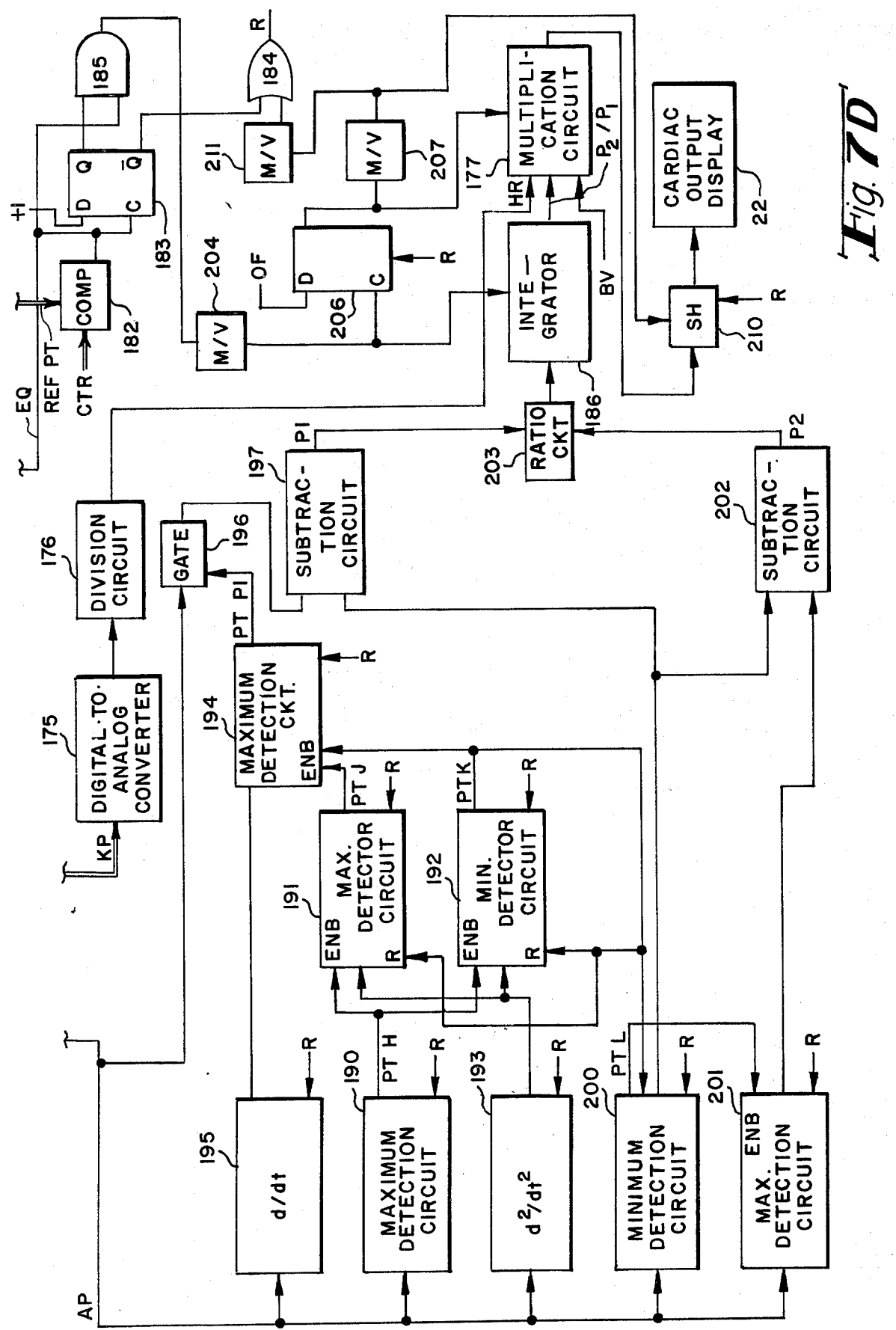

METHOD AND MEANS FOR MONITORING CARDIAC OUTPUT

BACKGROUND OF THE INVENTION

This invention generally relates to the measurement of blood flow and more particularly to the measurment of blood flow from the heart in a patient being aided by an intra-aortic balloon pumping system.

An intra-aortic balloon pumping system is used in the treatment of ischemic heart disease. The system includes a long slender balloon which is inserted surgically into a patient's descending thoracic aorta. An external system controller inflates and deflates the balloon in synchronism with the patient's heartbeat. The alternate inflation and deflation of the balloon boosts aortic diastolic pressure, lowers systolic pressure, and increases coronary blood flow. As a result, the balloon pumping system increases or maintains cardiac performance while reducing the workload on the patient's heart.

The monitor functions in response to the signals normally present in an intra-aortic pumping system: a pressure signal from a catheter in the radial artery and associated transducer, a balloon pressure signal representing the pressure within the balloon, and a balloon drive signal which controls the inflation or deflation of the balloon.

It is, of course, extremely desirable to measure the effectiveness of the balloon pumping system treatment. A key parameter in this regard is cardiac output, which is the total blood flow rate from the heart. Diverse, clinically acceptable methods for measuring cardiac output are used and other methods have been proposed.

The oldest and most reliable method is known as the Fick method. This method was first proposed in the late 1800's, but did not gain acceptance as a clinical method until procedures for cardiac catheterization were perfected. In accordance with this method, a catheter is implanted in the pulmonary artery to measure the oxygen concentration in venous blood while another catheter is implanted in the brachial, radial or femoral artery to measure the oxygen concentration in arterial blood. Patient oxygen comsumption is determined by breath analysis. The ratio of the differential of the arterial and venous blood oxygen concentrations to the patient oxygen consumption indicates cardiac output.

As can be appreciated, the Fick process is quite complicated and requires expensive apparatus. Even though it is recognized as being reliable, a dye method for determining cardiac output is now more popular. In accordance with this method, known since the late 1940's, a dye solution is injected through a catheter into the pulmonary artery. A constant flow blood sample is then withdrawn from another artery to provide a time analysis of dye concentration which leads to a determination of cardiac output. This method, although widely used, has two disadvantages. It is less accurate than the Fick method. Also, a patient may have an allergic reaction to the dye solution, so the method can not be used universally.

Another clinical method which has been used since the introduction of thermistors in the 1950's is a thermal dilution method. With this method, a cold saline solution is injected through a catheter into the right atrium. The dispersion of that solution is monitored by inserting a catheter with a thermister into the pulmonary artery. Cardiac output can then be determined by analyzing the temperature variations.

Other methods are experimental. In one such method, a magnetic flow meter is implanted in the ascending aorta. Leads from the flow meter are then connected to an external controller which indicates the blood flow at the flow meter. With still another experimental technique, a catheter implanted in the ascending aorta has means for obtaining spaced lateral pressure taps. The differential pressures from these taps indicate cardiac output.

All these foregoing clinical and experimental methods are invasive. Impedance plethysmography is an experimental non-invasive method. Energizing electrodes disposed on the skin are excited by an AC signal. Sensing electrodes, also on the skin, receive the signals and couple them to a controller which analyzes the exciting and receive signals for displaying cardiac output. Although this technique is non-invasive, the patient is subjected to electrical signals which, in some cases, may have deleterious effects.

When a patient is undergoing treatment by means of an intra-aortic balloon pumping system, all the foregoing methods for determining cardiac output require additional external or internal connections to be made to the patient. These connections can complicate treatment. None of the methods, other than the Fick method, produces an extremely accurate indication of cardiac output. As known, they are subject to rather substantial errors. Moreover, none of the clinical methods permit or facilitate continuous monitoring of cardiac output.

Therefore, it is an object of this invention to provide an improved method and apparatus for measuring cardiac output in a patient undergoing treatment by means of an intra-aortic balloon pumping system.

Another object of this invention is to measure cardiac output by using signals which are presently available in an intra-aortic balloon pumping system.

Still another object of this invention is to provide apparatus for measuring cardiac output continuously.

Yet another object of this invention is to provide apparatus for measuring cardiac output in an intra-aortic balloon pumping system without further invasion into the patient.

Still yet another object of this invention is to provide apparatus for measuring cardiac output which facilitates measurements and recording at the time the measurements are made.

SUMMARY

In accordance with this invention, a cardiac output monitor receives various system signals from an intra-aortic balloon pumping system including a signal representing the pressure in a patient's artery, normally the radial artery. The monitor determines the pressure which characterizes a ventricle ejection pulse and the pressure which characterizes the balloon deflation after a counterpulse. The monitor processes these signals and other system signals to indicate, on an interrupted or continuous basis, the patient's cardiac output.

This invention is pointed out with particularity in the appended claims. The above and further objects and advantages of this invention may be better understood by referring to the following description taken in conjunction with the accompanying drawings.

BRIEF DESCRIPTION OF THE DRAWINGS

FIG. 7, comprising FIGS. 7A through 7D, is an alternate embodiment of the cardiac output monitor shown in FIG. 4.

DESCRIPTION OF ILLUSTRATIVE EMBODIMENTS

Figure 1:
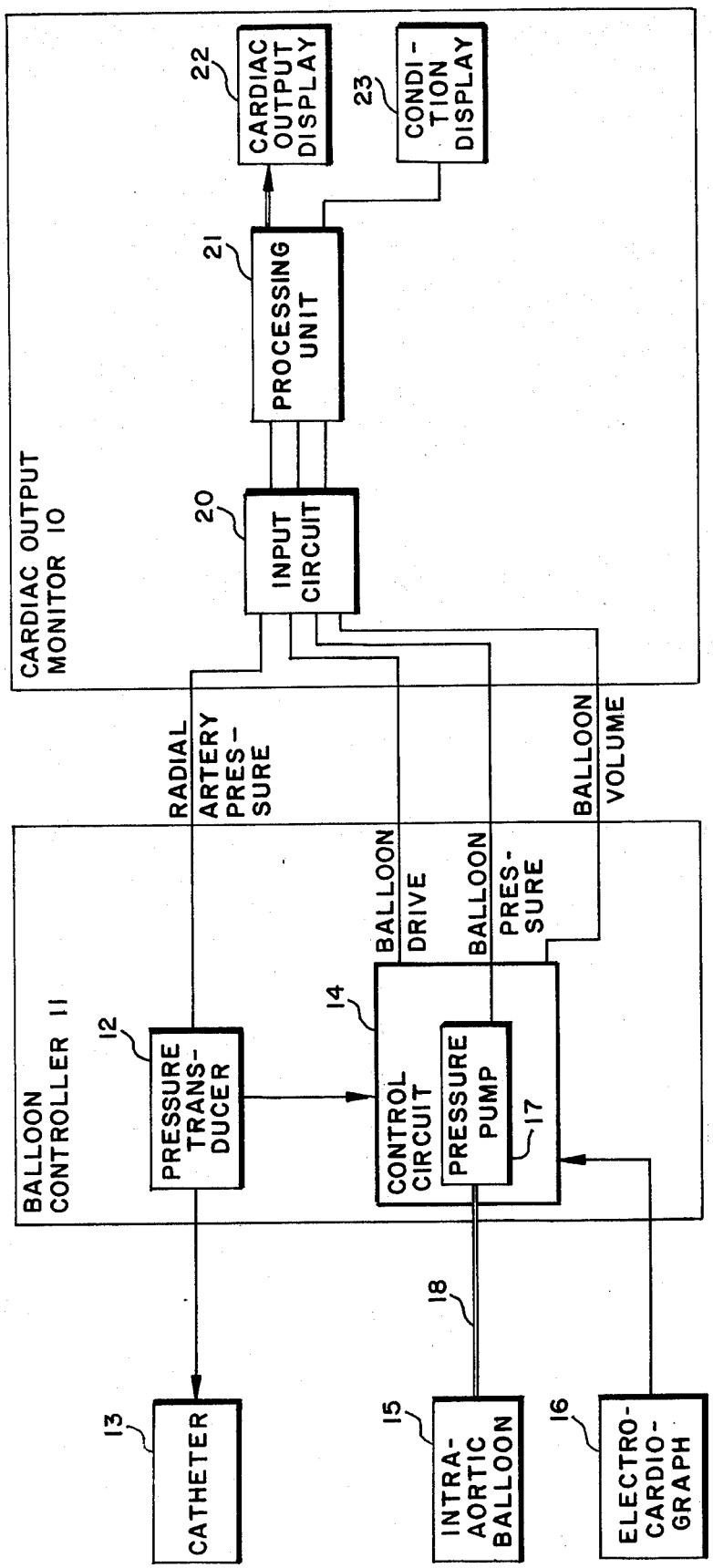
FIG. 1 is a diagram of a typical intra-aortic balloon pumping system utilizing this invention.
Figure 2A:
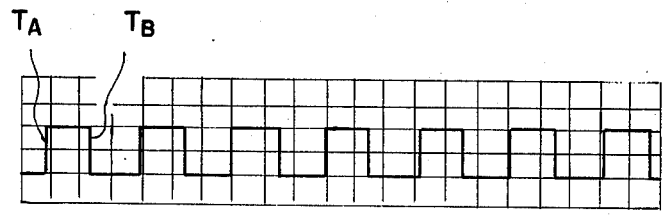
FIG. 2 comprises Graphs 2A through 2D of typical signals for a patient undergoing intra-aortic balloon pumping system treatment.
Figure 2B:
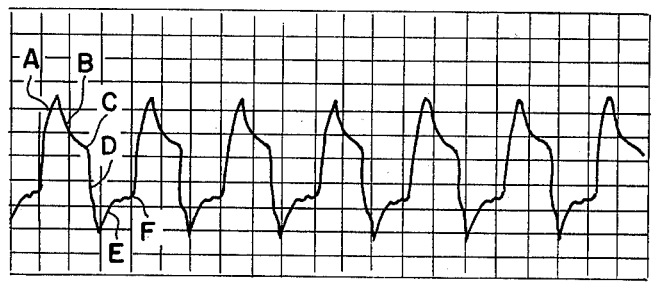
Figure 2C:
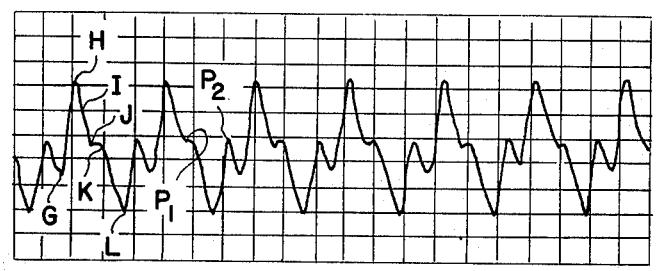
Figure 2D:
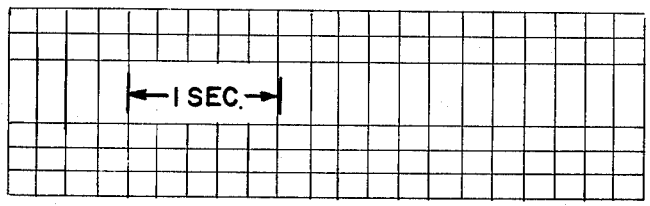

A cardiac output monitor 10 constructed in accordance with this invention is shown in FIG. 1. It connects to a balloon controller 11 which comprises a pressure transducer 12 for converting pressures received from a catheter 13, normally implanted in the radial artery, to an electrical radial artery pressure signal.

A control circuit 14 controls inflation and deflation of the intra-aortic balloon 15 on the basis of signals from an electrocardiograph 16. Typically, the control circuit 14 causes a pressure pump 17 of the diaphragm type to shift between first and second positions, thereby alternately to define two separate or distinct volumes within the pressure pump 17. Thus, when the control circuit 14 issues an inflation command, the pressure pump diaphragm shifts and reduces the volume in the pump to compress a gas, normally helium. The diaphragm remains in that position until a deflation command, whereupon the diaphragm retracts to its original position. As the pump 17 alternates between these positions, the gas in the intra-aortic balloon 15 and an interconnecting catheter 18 alternatively inflates and deflates the balloon 15.

Referring to FIG. 2, Graph 2A shows a typical BALLOON DRIVE signal wherein the patient has a heartbeat of about 96 beats per minute. The control circuit 14 in FIG. 1 transmits a positive signal to shift the pressure pump diaphragm to its first position at time $T_A$. As the catheter 18 in FIG. 1 constitutes a restricted flow orifice between the pump 17 and the balloon 15, the pressure within the balloon pump 17 rises rapidly over an initial portion A of the pressure curve shown in Graph 2B. During a portion B of the curve, the gas inflates the balloon 15 as the gas passes through the catheter 18. As the volume in the pump 17 is constant during this interval, the pump pressure decreases over the portion B. Then the rate of decrease slows at the point C of the curve as the pressure is determined by the back pressure of the blood in the patient's aorta.

When the controller 14 issues a deflation command, the balloon drive signal returns to zero as shown at $T_B$ in Graph 2A. The pressure pump 17 immediately shifts the diaphragm to its original position thereby to expand the pressure pump volume. The pressure in the pump 17 thus decreases rapidly over the curve portion D in Graph 2B. Then, as shown by portion E, the pressure in the pump 17 increases as the gas flows from the balloon 15 back through the catheter 18 into the pump 17. Finally, the curve portion F depicts the pressure of the deflated balloon just prior to the next inflation command.

As the pressure pump 17 receives successive BALLOON DRIVE signals and inflates the deflates the balloon 15, the blood pressure in the aorta and other arteries increases and decreases. Graph 2C depicts the corresponding pressure variations in a patient's radial artery. The time delay between the pressures in the balloon 15 and at the radial artery is due to the physiological make-up of the arterial tree.

Figure 3A:
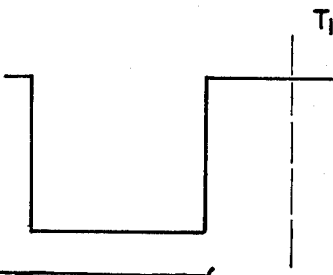
FIG. 3 comprises Graphs 3A and 3B of balloon drive and arterial pressure on an expanded scale which are useful in understanding this invention.

The BALLOON DRIVE and radial arterial pressure graphs shown in Graphs 2A and 2C, are shown in expanded form in FIG. 3, where Graph 3A depicts the BALLOON DRIVE signal while Graph 3B depicts variations in arterial pressure represented by an AP signal from pressure transducer 12 in FIG. 1. From point G through points H and I to J, the AP signal represents a pressure pulse produced when the balloon inflates. Once inflation has completed, the radial arterial pressure remains relatively constant or decreases slightly from point J to point K. Any loss in pressure results from displacement of blood in the aorta into other portions of the arterial tree. At point K, as the BALLOON DRIVE signal shifts, it produces a deflation pulse, represented by the AP signal excursion from point K to point L, as the pressure in the balloon 15 is reduced. This excursion is characterized by the pressure $P_1$. The AP signal from point L through $P_2$ to point G represents a ventricle ejection pulse. $P_2$ represents the maximum ventricle ejection pressure excursion relative to the minimum pressure at L.

In accordance with this invention, the pressure excursions at points $P_1$ and $P_2$ (as measured from the minimum pressure at L), the volume (BV) of the intra-aortic balloon 15, shown in FIG. 1, and the heart rate (HR), which can be determined during an analysis of the radial and arterial pressure or other system signals from the controller 11, are indicative of cardiac output. More specifically:

Cardiac output = $(P_2/P_1)$ (BV) (HR)

The ratio of the two pressures $P_2$ and $P_1$ leads to reliable estimates of the volume of blood ejected from the heart according to the above-mentioned formula.

Further, several observations about the AP pressure signal can be made. For example, the magnitude of the slope of the arterial pressure signal between points J and K is often very low, apparently because the flow of blood from the aorta during this interval is not reflected in a pressure change at the radial artery. $P_1$ occurs in time when various pressure pulse reflections in the system tend to cancel each other, so the pressure $P_1$ is relatively independent of these effects. Also the ratio $P_2/P_1$ generally has a value between 0.7 and 2 and often is close to unity so that problems introduced by non-linearities in the aortic compliance are minimized.

Figure 4:
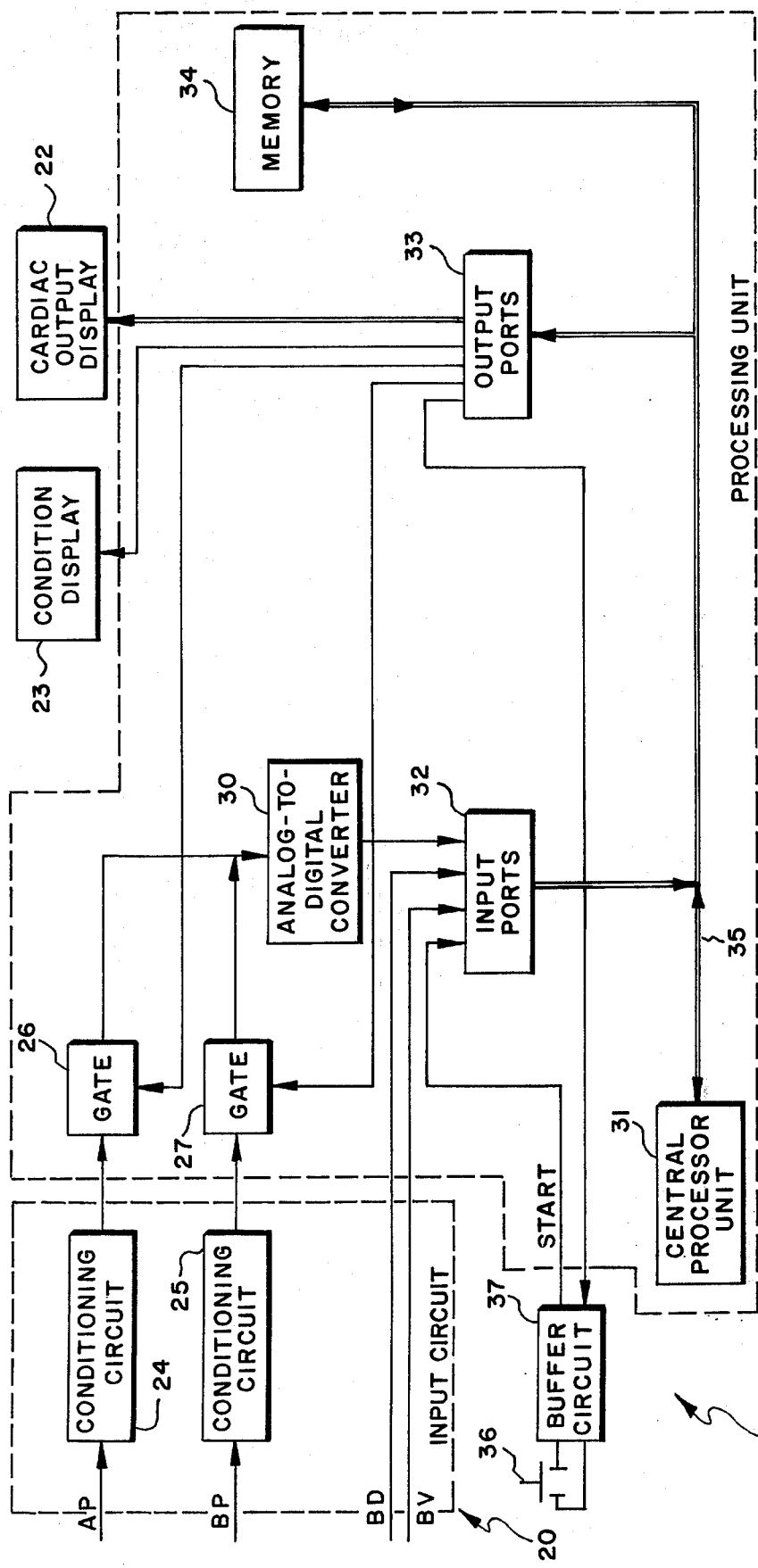
FIG. 4 is a block diagram of the cardiac output monitor shown in FIG. 1.

A preferred embodiment of the cardiac output monitor 10 is shown in FIG. 4. It includes an input circuit 20 for receiving the arterial pressure (AP), balloon pressure (BP), balloon drive (BD), and balloon volume (BV) signals; and a processing unit 21 for controlling a cardiac output display 22 and a condition display 23.

Conditioning circuits 24 and 25 in the input circuit 20 condition the analog AP and BP signals for use by the processing unit 21. It is assumed that the BD and BV signals are in proper binary form when they reach the processing unit 21, so they merely pass through the input circuit 20. If any conditioning of these signals is necessary, other condition circuits can be added to the input circuit 20. In the processing unit 21, gates 26 and 27 selectively couple the AP and BP signals respectively to an analog-to-digital converter 30. The converter 30 produces at its output a binary representation of its analog input.

The remaining elements in the processing unit 21 comprise a bus 35 that interconnects a central processor unit 31, input ports 32, output ports 33 and a memory 34. Specific embodiments of these elements 31 through 35 are described in "User's Manual, 8008 8-Bit Parallel Central Processor Unit" published by Intel, Corp. in 1973. For purposes of the present explanation, it is sufficient to know that the central processor unit 31 time-multiplexes address and data signals on the bus 35. In any reading or writing cycle, the central processor unit 31 first transmits address signals to select one of the input or output ports 32 or 33 or a location in the memory 34. Then the data is placed on the same bus for transfer either to or form the central processor unit 31. All data transfers are to or from the central processor unit 31. Thus, to transfer the BD signal to the memory 34, the central processor unit 31 first "reads" the data from an appropriate one of the input ports 32 and then "writers" the data into a specified location in the memory 34. In essence, the central processor 31 establishes various input and output paths and processes the input signals from the input circuit 20 to produce cardiac output signals for the display 22 and other signals for the condition display 23.

The operation of the processing unit 21 will be more fully appreciated by referring to the flow diagram of FIG. 5. Compiler statements and corresponding statement numbers for implementing this flow in the Intel 8008 central processor unit are also shown. These statements are converted into machine instructions for the central processor unit 31 by a compiler available from Intel Corp. As the correspondence between these complier statements and steps in the flow diagram will be apparent, there is no further discussion of these statements.

The processing unit 21 shown in FIG. 4 operates in two stages. In a first stage, depicted in FIGS. 5A and 5B, the cardiac output monitor stores periodic samples of the arterial pressure (AP) and the balloon drive (BD) signals in binary form. During the second stage, the processing unit 21 processes the sampled data and transmits output signals to the cardiac output display 22.

Figure 5A:
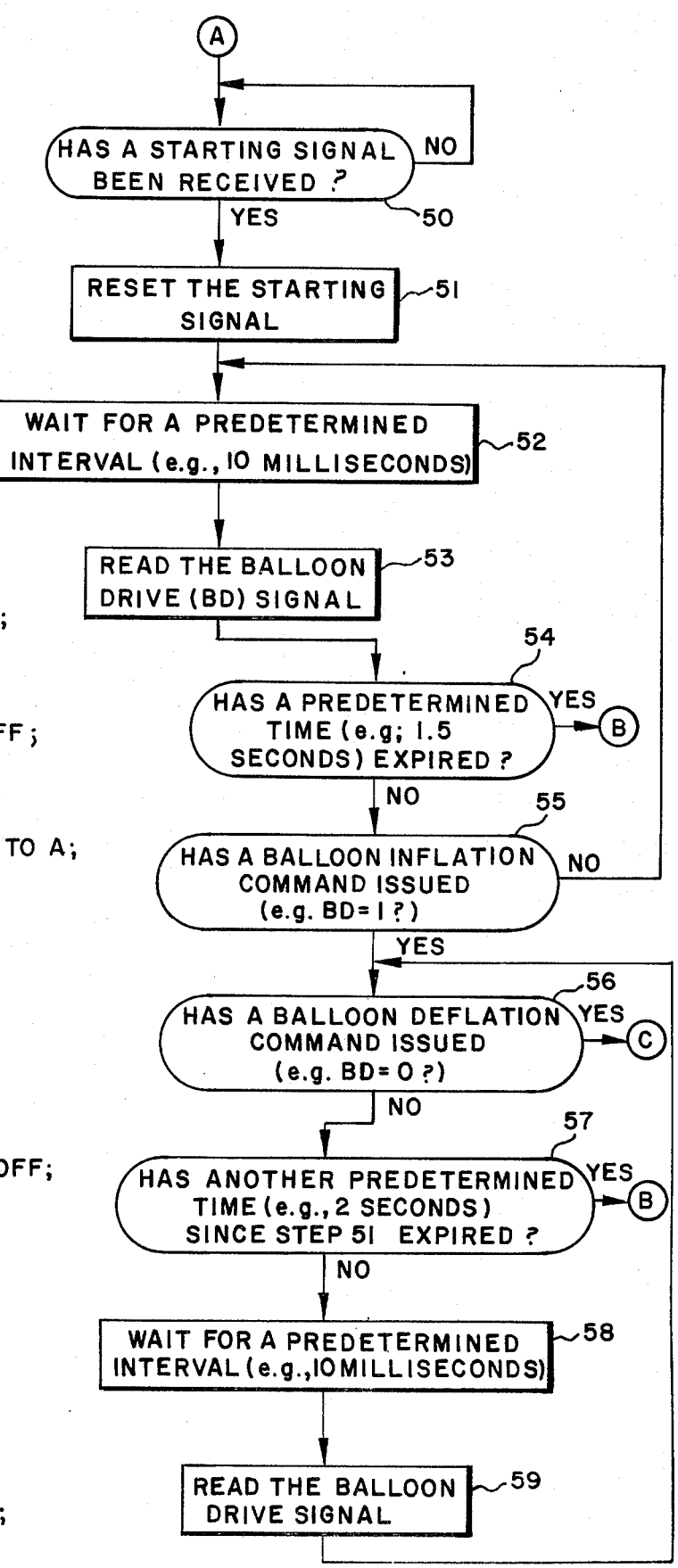
FIG. 5, comprising FIGS. 5A through 5I, includes a flow chart of a sequence for converting the incoming signals from an intra-aortic balloon pumping system to obtain signals representing cardiac output.

An operator obtains a reading of cardiac output by depressing a switch 36 in FIG. 4. A starting buffer circuit 37 then transmits a momentary or a continuous START signal to the input ports 32. As shown in FIG. 5A, the processing unit 21, while at rest, repeatedly couples the output from the buffer circuit 37 through one of the input ports 32 for testing (Step 50). When the switch buffer circuit 37 does transmit a START signal, Step 50 diverts to Step 51 which, in a monitor for taking a single sequence of readings, "resets" the starting switch by clearing the START signal from the buffer circuit 37. This is done by transmitting an output signal through the one of the output ports 33 connected to the buffer circuit 37. For continuous monitoring operations, Step 51 is eliminated.

Next, the processing unit 21 periodically samples the balloon drive (BD) signal until controller 11 (FIG. 1) issues a balloon inflation command, i.e., a BD signal transition from a ZERO level to a ONE level. Step 52 establishes the sampling interval while Step 53 transfers the BD signal through one of the input ports 32 to the unit 31. If the transition does not occur within a predetermined time (e.g., 1.5 seconds), Step 54 branches to point B, an entry to an OFF subroutine described later. Otherwise, Step 55 actually tests the BD signal for a transition.

Step 55 branches back to Step 52 until the balloon deflation command occurs, whereupon control shifts to Step 56. The balloon drive (BD) signal shifts to a ZERO level in response to the balloon deflation command, and this transition initiates the sampling operation. So long as the BD signal is at a ONE level, Step 56 branches to Step 57, which turns off the cardiac output monitor 10 (FIG. 1) if the balloon deflation command is late by branching to point B, the OFF subroutine. Step 58 determines the sampling interval and Step 59 transfer a new value of the BD signal through the input ports 32 before returning the operation to Step 56.

Figure 5B:
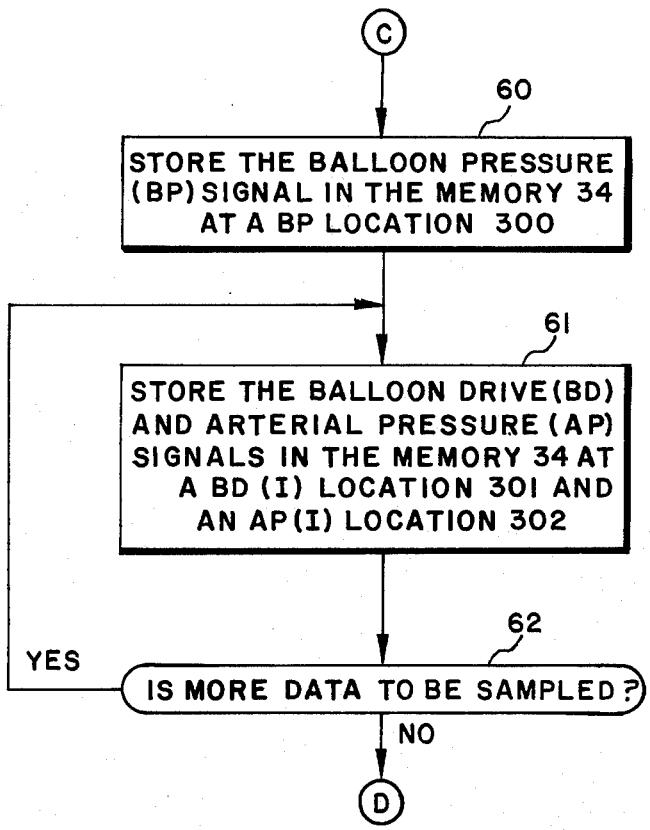
Figure 6:
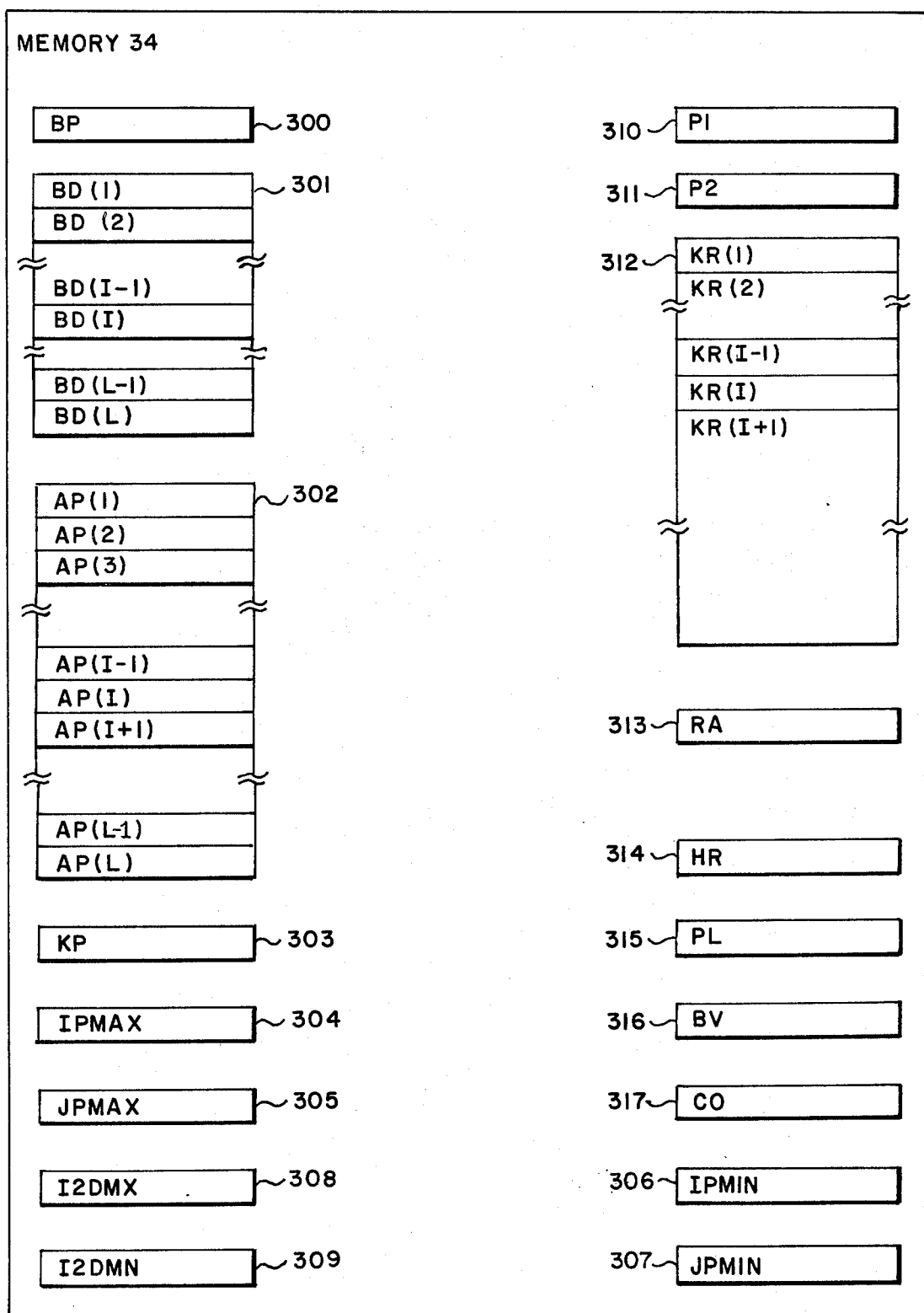
FIG. 6 is a memory map for the monitor in FIG. 4.

When the controller 11 in FIG. 1 issues a balloon deflation command within the time interval, Step 56 branches to point C in FIG. 5A and to Step 60 in FIG. 5B whereupon the sampling operation begins. Initially, the processing unit 21, in Step 60, enables the gate 27 to transfer the BP signal to the analog-to-digital converter 30 and the digital representation of the balloon pressure to a BP location 300 (FIG. 6) in the memory 34 through the input ports 32. Then, by processing Steps 61 and 62 iteratively, the processor unit 31 transfers the balloon drive signal and the digital representation of the arterial pressure signal into a series of BD (I) and AP(I) memory locations 301 and 302, respectively (FIG. 6). When the samples are stored, Step 62 diverts to point D and Step 63 in FIG. 5C which is the first step in the second operating stage for processing the sampled data to obtain and display cardiac output. When the processing unit 21 completes the stage depicted in FIGS. 5A and 5B, the memory 34 (FIG. 6) stores in the locations 300, 301, and 302 data in binary form corresponding to the arterial pressure and balloon drive over a measurement interval (e.g., 5 seconds) and balloon pressure at the beginning of the measurement interval. Thus, the memory 34 constitutes an historical model of patient conditions during the measurement interval.

Figure 5E:
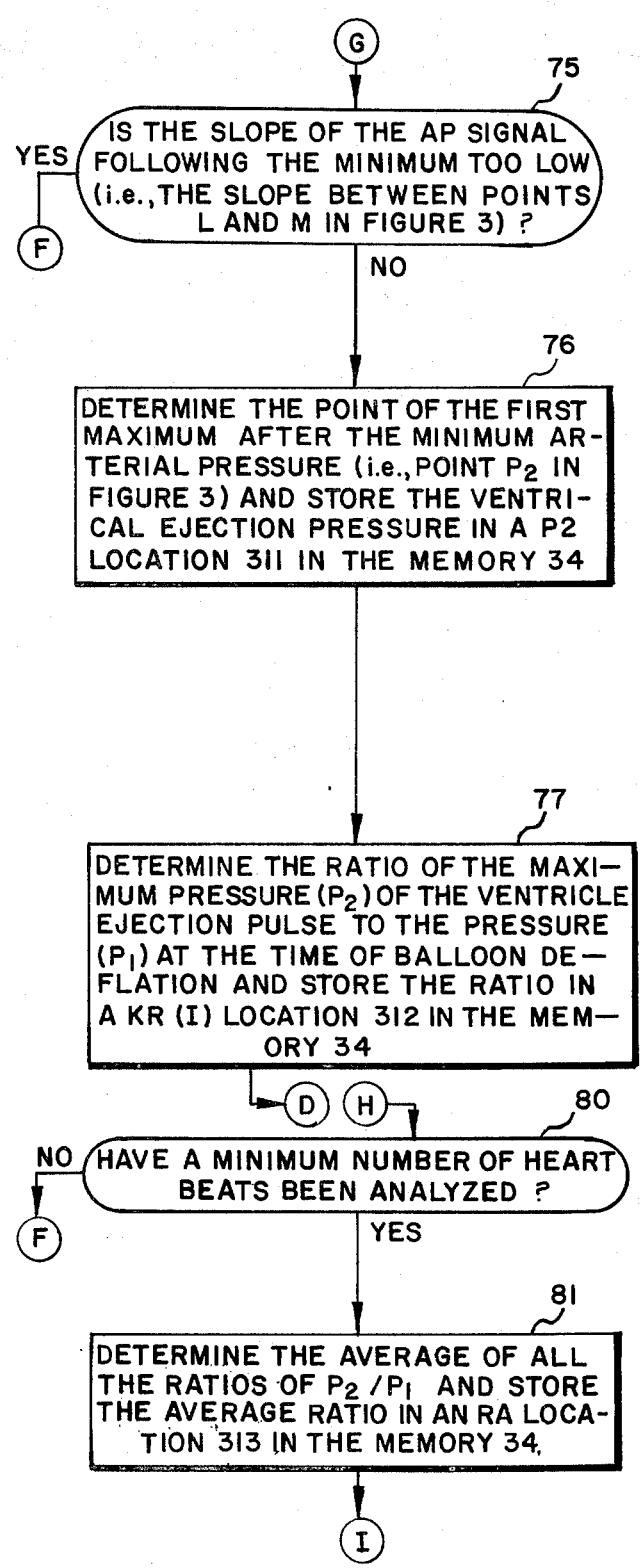

In this specific embodiment, the balloon deflation pressure $P_1$ and the ventricle ejection pulse pressure $P_2$ obtained for each heartbeat in succession are stored in the memory 34 in Steps 63 (FIG. 5C) through 77 (FIG. 5E). Step 63 locates the $T_1$ and $T_2$ times thereby to define a beat interval over which the radial artery pressure is analyzed and increments the value in a KP location 303 (FIG. 6) thereby to count the number of heartbeats. Normally Step 64 branches to Step 65 to ascertain the location of the first maximum of arterial pressure which is point H in Graph 3B. After the location of minimum arterial pressure is found (point L in Graph 3B) in Step 66, the memory 34 (FIG. 6) contains the locations of and values of the maximum and minimum pressures at locations 304 through 307.

If the magnitude of the slope of the AP signal between points H and I (Graph 3B) is not below a predetermined level, the AP signal may be noisy, system timing may be incorrect, the catheter 13 in FIG. 1 may be defective or some other problem may exist. Step 70 diverts to a Step 94 in FIG. 5G to indicate that a problem exists. Otherwise, the processing unit 21, in Step 71, obtains the second order differential of the AP signal.

The maximum and minimum of the second order differential signal define points J and K in Graph 3B. In Step 72, the processing unit establishes these points and stores the locations in 12DMX and 12DMN locations 308 and 309 (FIG. 6). As previously discussed, the AP signal defines a plateau between points J and K in Graph 3B. If a systm problem exists, then the AP signal may be low or its plateau slope in this region may not be within a normal range of values. In Step 73 the processing unit 21 tests the magnitude of the AP signal and its slope and branches to Step 94 in FIG. 5G if a problem exists.

Figure 3B:
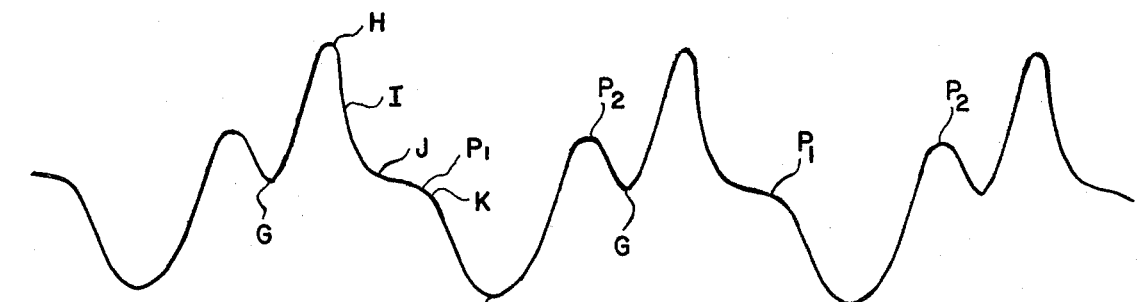

Assuming the AP signal slope is normal, the processing unit, in Step 74, locates point $P_1$ in FIG. 3B as a point of minimum slope between points J and K. The value $P_1$ which represents the balloon deflation excursion pressure to the minimum pressure at point L, is stored in a $P_1$ location 310 (FIG. 6).

After this point is obtained, the processing unit 21 again checks the system operation by examining the slope of the AP signal between points L and M in Graph 3B. If the slope is too low, Step 75 in FIG. 5E branches to Step 94 in FIG. 5G. Otherwise, the processing unit 21 uses Step 76 to locate the next maximum of the AP signal which corresponds to the maximum pressure of the ventrical ejection pulse. Then the processing unit 21 determines the difference between this pressure and the minimum pressure at point L in Graph 3B and stores the difference in a $P_2$ location 311 (FIG. 6).

In step 77, the processing unit 21 retrieves the numbers from location 310 and 311, determines the ratio, and stores the ratio for that heartbeat in a KR(I) location 312 in the memory 34 of FIG. 6. Then the processing unit 21 returns to Step 63 to initiate an operation for a successive heartbeat. When all the data stored in locations 301 and 302 of FIG. 6 corresponding to the last sampled heartbeat has been converted, Step 64 in FIG. 5C branches to Step 80 in FIG. 5E. At this time the KP location 303 has a number representing the number of sampled heart beats; the BP location 300, the initial balloon pressure; and each KR location 312, the $P_2/P_1$ ratio for a heartbeat.

In Step 80 (FIG. 5E) the processing unit 21 determines whether the number in the KP location 303 (FIG. 6) represents a minimum number of heart beats which should be sampled. Step 80 then branches to Step 94 in FIG. 5G to indicate a problem or to Step 81 in FIG. 5E.

In Step 81, the processor unit 21 retrieves all the ratios from the KR locations 312 (FIG. 6), obtains an average value for the ratios, and stores the average ratio in an RA location 313 (FIG. 6). The processing unit 21 might, as an alternative, obtain the median of the ratios. In the following "average" includes either the average or "median" value. The ratio is reduced if it is larger than a predetermined maximum in Steps 82 and 83 in FIG. 5F. It is assumed that the aorta and the rest of the arterial tree constitute a linear fluidic system. In fact, they do not. If, in a particular patient, the $P_2/P_1$ ratio becomes overly large, the effect of non-linearities must be corrected by reducing the ratio by a fixed percentage.

In Step 84, processing unit 21 retrieves the value stored in the KP location 303 of FIG. 6 to calculate the heart rate based upon the number of recorded beats and the timing interval. An HR location 314 (FIG. 6) stores this heart rate value.

Steps 85 and 86 perform another check on system conditions. In step 85 the processing unit 21 determines the average plateau width between points J and K in FIG. 3 and normalizes the average width with respect to the heart rate. A PL location 305 (FIG. 6) receives the normalized plateau width value. If this value is too large, the processing unit 21, in Step 87, energizes a timing light in the condition display 23 (FIG. 4) to indicate to the operator that the deflation commands are late.

Intral-aortic ballons have known volumes. In Step 88, the processing unit 21 couples the BV signals through the input ports 32. In one embodiment, the BV signals are in the form of a code which the processing unit converts into a balloon volume value for storage in a BV location 316 (FIG. 6).

Figure 5F:
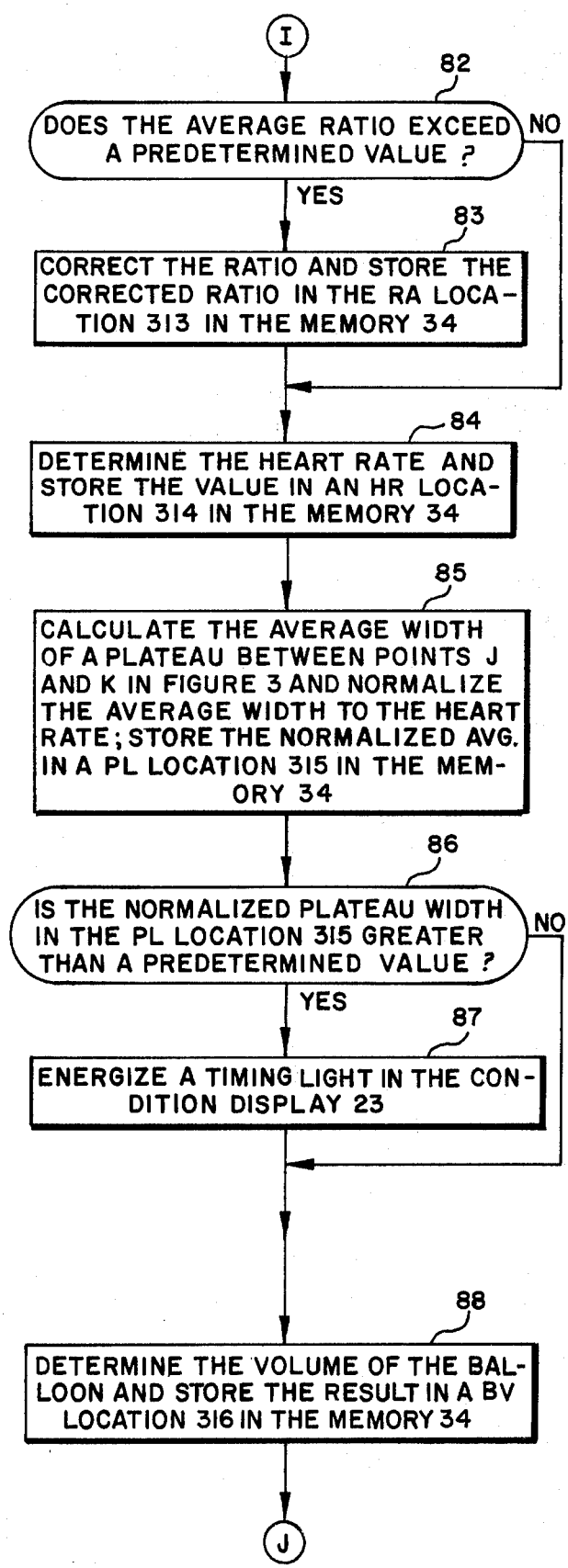

When the processing unit 21 completes Step 88 in FIG. 5F, the BP, RA, HR and BV locations 300, 313, 314 and 316 contain all the values for calculating the cardiac output (CO) according to the equation $$CO = (P_2/P_1)(BV)(HR)$$

This calculation is performed in Step 89 (FIG. 5G) and a CO location 317 (FIG. 6) stores this result. If the value of CO is overly large, the processing unit 21, in Step 90, diverts to Step 94 to indicate a system problem.

The actual inflation volume of a balloon depends upon the current pressure in the aorta (i.e., aortic back pressure) against which the balloon must fill. In accordance with another aspect of this invention, the magnitude of the pumped balloon volume (BV) is increased or decreased about 1.5 c.c. for each 10 millimeters of pressure below or above 75 millimeters of pressure, respectively, to substantially correct the effect for the aortic back pressure. After the processing unit 21 makes this correction in Step 91, it transfers the signals transmitted by the CO location 317 (FIG. 6) through the output ports 33 in FIG. 4 to the cardiac output display 22 in Step 92. Then the processing unit 21 returns to Step 50 in FIG. 5A. If the switch 36 and buffer 37 transmitted a momentary START signal, the processing unit 21 awaits a subsequent START signal. However, if the START signal is continuous, Step 50 immediately and automatically diverts to Step 52 (Step 51 is omitted). Such continuous operations are beneficial when the display 22 is a chart recorder, for example. In such an application, the switch 36 could be integral with a jack in the monitor which receives a chart recorder plug.

If the tests performed at Steps 54 and 57 in FIG. 5A indicate no changes in the BD signal for the predetermined periods, it is assumed that the intra-aortic balloon pumping system is off. The processing unit 21, in that case, diverts to Step 93 in FIG. 5G and transfers ZERO values through the output ports 33 to the cardiac output display 22 in FIG. 4. A display of ZERO therefore indicates that the system is off.

Figure 5G:
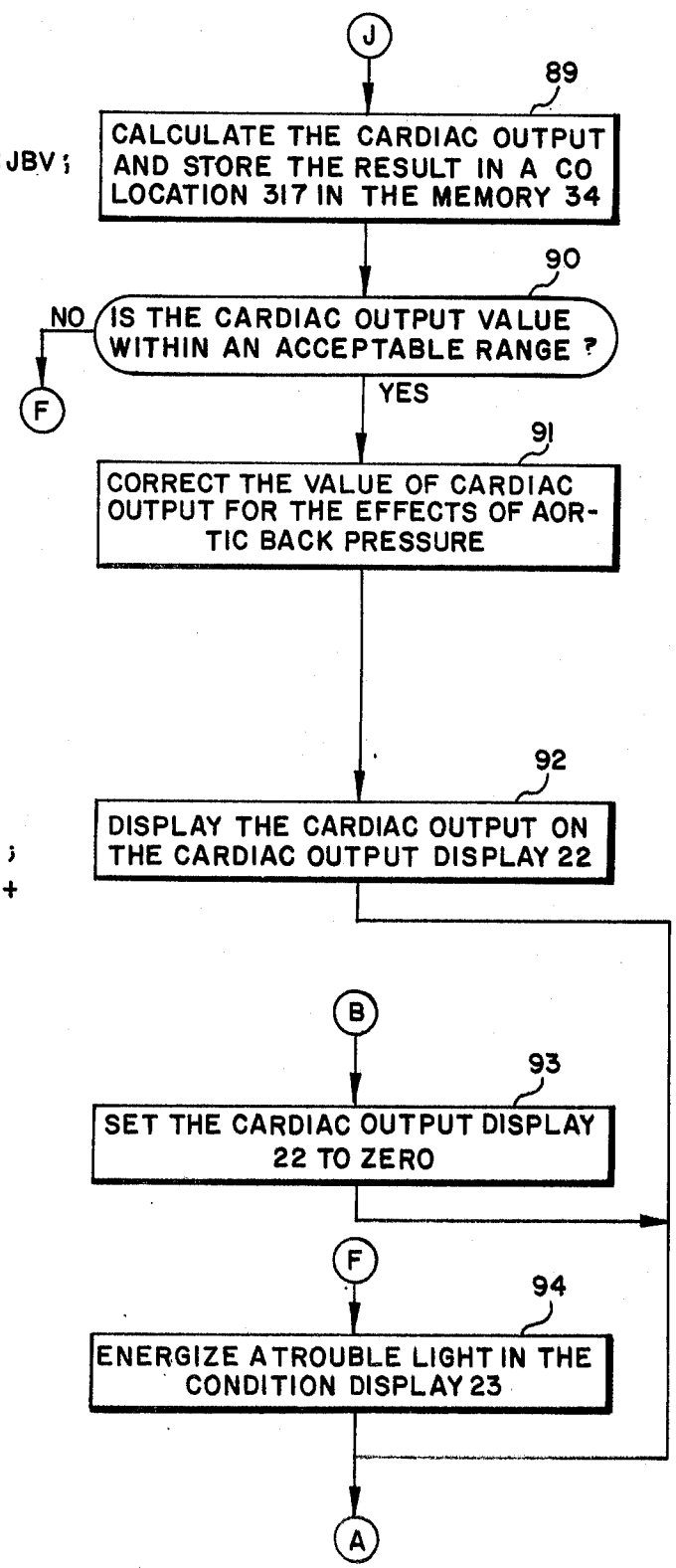

Similarly, if any test performed at Steps 70 and 73 in FIG. 5D, Steps 75 and 80 in FIG. 5E and Step 90 in FIG. 5G is failed, the processing unit 21, in Step 94, passes to the condition display 23 signals which energize a trouble light thereby to alert the operator of some improper condition.

FIGS. 5H and 5I contain various compiler statements which constitute the subroutines for finding a maximum, a minimum and the timing points. Further, the statements required by the compiler language for declaring variables are also shown. As they are straightforward statements, they are not discussed further.

Thus, this embodiment of the invention provides a number of advantages. First, the cardiac output is obtained without any further connection to a patient as all the input signals are available from the intra-aortic balloon pumping system. The resulting cardiac output is reasonably reliable, and the results, in clinical conditions, compare favorably with results obtained from using the standard clinical tests for cardiac output. In addition, the system can continuously measure and display cardiac output unlike present clinical methods. Moreover, the monitor provides information about system conditions more rapidly than can be obtained by operator observation.

FIG. 4 discloses a specific embodiment of the invention which uses advanced microprocessor techniques. However, other implementations of this invention are also possible. FIG. 7 depicts in basic block form one such circuit comprising various conventional analog and digital circuitry.

Figure 7B:
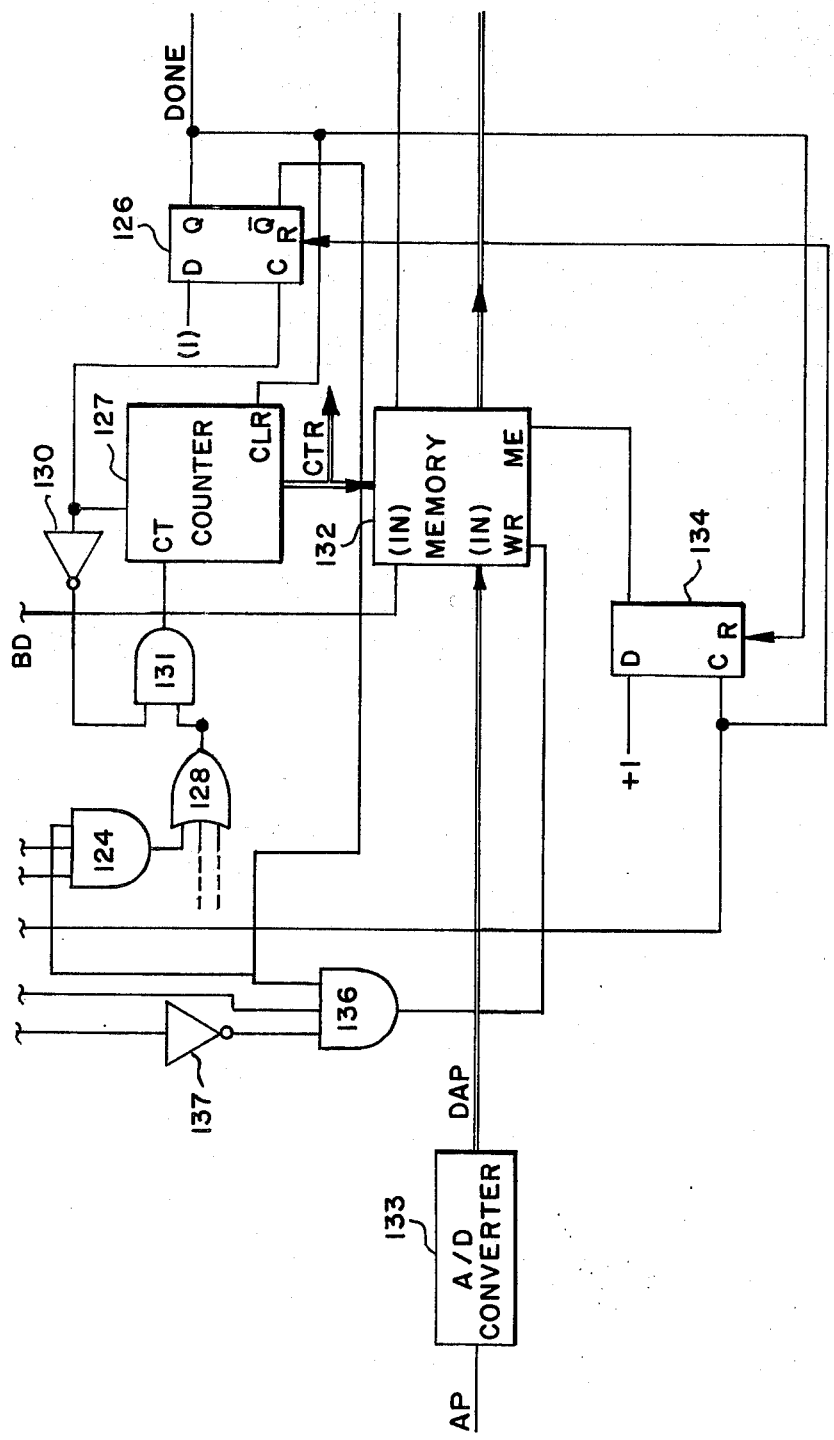

The circuitry in FIGS. 7A and 7B samples AP and BD signals and stores the sampled data in a memory for subsequent analysis by the circuitry in FIGS. 7C and 7D. Assuming a BUSY latch 100 in FIG. 7A is reset, a START signal passes through AND gate 101 to clear BP register 102 and energize an OR gate 103. The OR gate 103 enables an AND gate 104 to pass clocking pulses of about 50% duty cycle from a pulse generator 105 to an AND gate 106. The first such pulse from the AND gate 104 sets the BUSY latch 100. An inverter 108 and flip-flop 109 block the first pulse from the pulse generator 105. However, the trailing edge of that pulse sets the flip-flop 109 to enable the AND gate 106 and latch the circuit in FIG. 7A until a DONE signal is transmitted. Then the second and subsequent pulses pass through the AND gate 106 to trigger a monostable multivibrator 110. The pulses from the generator 105 and multivibrator 110 overlap so an AND gate 111 triggers a monostable multivibrator 113 when the BD signal shifts to a ONE level. An AND gate 114 receives the output from the multivibrator 113 as well as the pulses from the pulse generator 105, an inverted BD signal from an inverter 115 and the Q̄ signal from a flip-flop 116. Thus, the flip-flop 116 sets whenever it is reset and the BD signal shifts to a ZERO level. The output signal, a BD=0 signal, enables the remaining portions of the circuit to begin reading data into memory. Thus, these circuit elements in FIG. 7A function in accordance with FIG. 5A.

Once the BD signal shifts to ZERO, the BD=0 signal enables an AND gate 120 to pass subsequent clock pulses from the pulse generator 105. A flip-flop 121, set by the output from the AND gate 101, also enables the AND gate 120. The first pulse from the AND gate 120 clocks into the BP register 102 a digital representation of the balloon pressure (BP) signal supplied from an analog-to-digital converter 122. An inverter 123 clocks the flip-flop 121 to a reset condition on the trailing edge of that pulse to disable the AND gate 120.

Pulses from the pulse generator 105 also pass through another AND gate 124 in FIG. 7B. A flip-flop 125 in FIG. 7A, set on the leading edge of the clocking pulse to the BP register 102, and the reset output of a DONE flip-flop 126 in FIG. 7B, which the AND gate 120 resets, enable the AND gate 124.

The clocking pulses thus passed by AND gate 124 advance a counter 127 through an OR gate 128. The counter 127 has a modulus which is two times the number of samples to be taken and an inverter 130 couples the signal from the most significant bit position to an AND gate 131 between the OR gate 128 and the counter 127. Initially the counter 127 contains ZERO, so the AND gate 131 is enabled. The remaining CTR signals from the counter 127 constitute address signals for a memory 132.

The memory receives, as data inputs, the BD signal and the binary representations of AP signals from an analog-to-digital converter 133. A writing flip-flop 134, set in response to a pulse from the AND gate 120, conditions the memory 132 for writing operations. An AND gate 136 provides the clocking pulses to write the data into the memory 132. The AND gate 136 passes delayed clocking pulses from an inverter 137 when the flip-flop 125 is set and the DONE flip-flop 126 is reset. Thus, during the first half of a clock pulse interval from the pulse generator 105, the data to be written and addressing signals are coupled to the memory 132, while the data is written into the memory 132 during the second half of the clock pulse interval.

When the counter 127 produces a ONE in the most significant bit position, all the required samples have been taken and the functions of FIG. 5B are completed. Then the inverter 130 disables the AND gate 131, so no further operations can occur. This shift in the most significant bit also sets the DONE flip-flop 126. The DONE signal resets the flip-flop 134 so no further writing operations can occur and disables the AND gates 124 and 136. Thus, when the flip-flop 126 transmits the DONE signal, the memory 132 constitutes an historical model of data sampled during the sampling interval. The data is all in a binary form and corresponds to the arterial pressure and balloon drive signals.

FIGS. 7C and 7D disclose the circuitry for processing the information in the memory 132. Certain elements, including the counter 127 and the memory 132, are also shown in FIG. 7C. When an element is shown twice in FIG. 7, it is identified by the same reference numeral.

Now referring to FIG. 7C, the DONE signal triggers a monostable multivibrator 140 and clears the counter 127 so the inverter 130 enables the AND gate 131. The DONE signal also enables an AND gate 150 to couple clocking pulses from another clock 151 through the OR gate 128 to advance the counter 127. The clock 151 has a much greater frequency than the pulse generator 105 in FIG. 5A; for example, the pulse generator 105 could have a frequency of 100 Hz and the clock 151, 500 kHz.

The circuitry in FIGS. 7C and 7D analyzes the data in two stages. In a first stage, the reference points, such as $T_1$ and $T_2$ in FIG. 3, are located. More specifically, as the counter 127 advances, a monostable multivibrator 154 is connected to transmit a pulse at each transition of the BD signal and clock a JK flip-flop 155. As the first location in the memory 132 always contains a ZERO and the flip-flop 155 is reset by the DONE signal, the flip-flop 155 always reflects the binary state of the BD signal. A delay circuit 156 couples each pulse from the multivibrator 154 to routing AND gates 157 and 160. Thus, when the flip-flop 155 sets, the AND gate 157 clocks a register 161 to store the CTR signals from the counter 127 corresponding to the occurrance of a positive transition of the BD signal. Likewise, a register 162 stores the CTR signals corresponding to the occurrence of a negative transition.

The output from a delay circuit 163 energizes an AND gate 164 whenever the flip-flop 155 is reset to produce a writing operation in a reference point memory 165. Thus, immediately after the register 162 stores a transition location, the AND gate 164 causes the reference point memory 165 to store data in a location defined by a clock counter 166. The stored data is from a parallel adder circuit 167 which sums the numbers in the registers 161 and 162. In a simple circuit, the sum is shifted to the right by the interconnection between the adder 167 and the memory 165 so the memory 165 stores an approximation of the average value of these two numbers. The leading edge of each pulse from the multivibrator 154 passes through an OR gate 170 to advance the counter 166. It always points to an empty location in the reference memory 165 before the AND gate 164 produces a writing pulse. Thus, when the counter 127 transmits the OF signal, the reference point memory 165 contains all the transition point locations, and the counter 166 also contains a number which represents the number of heart beats which were recorded. Assuming that the balloon drive signals and the heart beat are synchronized, this number reflects the true heart rate over the measured interval, which is fixed by the counter 127.

The pulse from the multivibrator 140 clears a flip-flop 172 and passes through an OR gate 141 to clear the counter 127 at the beginning of the reference point location stage. The flip-flop 172 thereby enables the AND gate 150 and disables an AND gate 180 during this stage. Another AND gate 142 is enabled by the DONE signal and sets the flip-flops 172 in response to signals at the end of this stage thereby disabling the AND gate 150 and the multivibrator 154 while enabling the AND gate 180. At the same time, the flip-flop 172 triggers a monstable multivibrator 172 to clear the counter 127 through the OR gate 141 and to load the heart beat number in the counter 166 into a KP register 174 and enables a digital-to-analog converter 181. Thereafter clock pulses from the AND gate 180 advance the counter 127 to produce a sequence of CTR signals at the input to the memory 132. Thus, the AP signal from the memory 132 changes at the clock rate and the digital to analog converter 181 produces an analog representation of the arterial pulse pressure for analysis as the counter 127 advances at the rapid clock rate. No change in the contents of the memory can occur as the flip-flop 134 in FIG. 7B is reset.

Referring to FIG. 7D, no analysis occurs until a comparator 182 sets a flip-flop 183, since the $\overline{Q}$ signal from the flip-flop 183 energizes an OR gate 184 to produce a resetting (R) signal applied to all the analog circuits in FIG. 7D. The comparator 182 receives the CTR signals from the counter 127 (FIG. 7C) and the REF PT signals from the memory 165, initially the address of the first reference point $T_1$ in FIG. 3B. When the counter 127 reaches that address, the comparator 182 transmits an EQ signal thereby setting the flip-flop 183 and terminating the resetting (R) signal. An AND gate 185 is not energized because the output from the comparator 182 immediately advances the counter 166 (FIG. 7C) to the next address, so the equality ceases immediately. Thus, an integrator 186 is not enabled, and a zero condition exists at the output of the integrator.

However, with the flip-flop 183 in FIG. 7D set, circuits for analyzing various characteristics of the AP signal by analog techniques become operative. These include a maximum detection circuit 190 which transmits a PT H signal which corresponds to point H in FIG. 3. The PT H signal enables a maximum detection circuit 191 and a minimum detection circuit 192 which receive the output from a second order-differential circuit 193. This circuit 193 transmits a signal corresponding to $d^2AP/dt^2$. Point J (FIG. 3) is characterized in that the second order differential is a maximum at that point so the maximum detection circuit 191 transmits a PT J signal indicating a beginning of the plateau region. This signal enables a maximum detection circuit 194 until the circuit 192 detects a minimum which is characteristic of point K in FIG. 3. While the circuit 194 is enabled, it transmits a PT P1 signal when a signal from a first order differential circuit 195 is a maximum. The PT P1 signal enables a gate 196 to couple the AP signal to an analog subtraction circuit 197. Additionally, the PT K signal resets the detector circuits 191 and 192.

A minimum detection circuit 200 enabled by the PT K signal, transmits a PT L signal when the next following minimum of the AP signal is detected. This signal enables a maximum detection circuit 201, which provides the maximum pressure of the ventricle ejection pulse at point $P_2$. The pressure signal at point L is coupled from the minimum detection circuit 200 to the subtraction circuit 197 and a subtraction circuit 202 which receives the signal from the maximum detection circuit 201 corresponding to point $P_2$ in FIG. 3. Both circuits 197 and 202 contain any necessary sample and hold circuits. Thus, the minimum pressure at point L is subtracted, and the outputs from the circuits 197 and 202 represent the pressure excursions at the balloon deflation command ($P_1$) and at the maximum pressure of the ventricle ejection pulse ($P_2$), respectively. A ratio circuit 203 produces an input to the integrator 186 corresponding to the $P_2/P_1$ ratio for the heartbeat.

When the counter 127 identifies the location corresponding to the next reference point in the memory 165, the comparator 182 energizes the AND gate 185 and triggers a monstable multivibrator 204 to energize the integrator 186 for a fixed interval. The integrated value is an input to the multiplication circuit 177, but a sample and hold circuit 210 does not respond to the output signal. Thus, the output from the sample and hold circuit 210 corresponds to the sum of the $P_2/P_1$ ratios for each heartbeat.

This operation continues for each additional heartbeat until the counter 127 again transmits the OF signal. A flip-flop 206 sets and turns on the multiplication circuit 177 which also receives the HR signal from the division circuit 176 and the BV signal which is transmitted by conventional means. When the flip-flop 206 sets, it also triggers a monstable multivibrator 207 which enables the sample and hold circuit 210 for a predetermined period of time. The circuit 210 energizes the cardiac output display 22 to indicate blood flow. Then the trailing edge of the pulse from the multivibrator 207 triggers another monostable multivibrator 211 to transmit a resetting (R) pulse from the OR gate 184.

FIG. 7 shows only the circuitry for providing a cardiac output signal for the display 22. It will be apparent, however, that the additional circuits can be added to detect various conditions previously described with respect to the system in FIGS. 4 and 5. It will be apparent that other analysis methods are possible. For example, the KP register 174 in FIG. 7 7C could be replaced by a counter incremented by each pulse from the multivibrator 204 in FIG. 7D thereby to record heart beats. Still other circuit variations are possible.

Therefore, two basic embodiments of this invention for producing an indication of cardiac output in an intra-aortic balloon pumping system are disclosed. In both embodiments all the incoming signals are obtained from the balloon pumping system and controller. The embodiments are described with respect to specific components including a particular central processor unit, and, in FIG. 7, certain circuit arrangements. However, it will be apparent to those skilled in the art that the circuitry and specific operation of both embodiments can be altered. Both embodiments disclose a measurement system in which each display is effected manually. Automatic operations can be obtained by the disclosed simple modification to the circuitry in FIG. 4 or a like modification to the circuitry in FIG. 7. Therefore, it is the object of the appended claims to cover all such variations and modifications as come within the true spirit and scope of this invention.

What we claim as new and desire to secure by Letters patent of the United States is:

1. Cardiac output apparatus for connection to an intra-aortic balloon pumping system including a balloon located in a patient's aorta which is alternatively inflated and deflated in synchronism with the heart to improve blood flow therefrom, said apparatus displaying the quantity of blood flow in the patient's heart in response to a signal representing blood pressure in an artery and including:
   A. pressure signal means for transmitting an input pressure signal in response to the blood pressure signal from the system,
   B. means for transmitting a balloon deflation signal representing a pressure excursion at the time the balloon is deflated in response to the input pressure signal,
   C. means for transmitting a ventricle ejection pressure signal representing the pressure excursion during a ventricle ejection pulse in response to the input pressure signal,
   D. means responsive to the balloon deflation pressure and the ventricle ejection pressure signals for transmitting an output signal representing blood flow from the aorta, and
   E. means for utilizing the output signal.

2. Cardiac output apparatus as recited in claim 1 wherein the balloon pumping system transmits a balloon drive signal to control balloon inflation and deflation, said apparatus additionally including timing means responsive to the balloon drive signal for transmitting an input timing signal, said ventricle ejection and balloon deflation pressure signal transmitting means and said signal transmitting means being responsive to the input timing signal.

3. Cardiac output apparatus as recited in claim 2 additionally comprising means for transmitting balloon pressure signals representing the pressure in the balloon when the balloon drive signal initiates balloon deflation, said output signal means being response to the balloon pressure signals for modifying the cardiac output signal.

4. Cardiac output apparatus as recited in claim 1 wherein said output signal transmitting means includes means for transmitting a ratio signal in response to the ventricle ejection pressure and balloon deflation pressure signals.

5. Cardiac output apparatus as recited in claim 1 additionally comprising means for transmitting balloon volume signals corresponding to the volume of the balloon and wherein said output signal transmitting means includes means for receiving balloon volume signal and means for transmitting as the output signal a cardiac output (CO) signal in accordance with $$CO = (p_2 P_1)(HR)(BV)$$

wherein $P_2$ corresponds to the ventricle ejection pressure signal, $P_1$ corresponds to the balloon deflation pressure signal, BV corresponds to the balloon volume and HR corresponds to the heart rate, said apparatus additionally comprising means for transmitting a heart rate signal.

6. Cardiac output apparatus as recited in claim 5 wherein said means for transmitting the balloon deflation pressure and ventricle ejection pressure transmit a new set of said signals for each heart beat, and said cardiac output transmitting means includes means for transmitting a final ratio signal based upon the ratios of said pressure signals for each heart beat.

7. Cardiac output apparatus as recited in claim 5 additionally comprising input pressure analysis means for indicating abnormal conditions in response to predetermined characteristics of the input pressure signal.

8. Cardiac output apparatus as recited in claim 5 wherein the input pressure signal is characterized by a plateau region in the vicinity of point of balloon deflation, said cardiac output apparatus additionally comprising plateau analysis means connected to said output means for indicating abnormal conditions in response to predetermined characteristics of the input pressure signal in the plateau region.

9. Cardiac output apparatus as recited in claim 8 wherein said plateau analysis means is responsive to a signal representing the magnitude of the input pressure signal in the plateau region.

10. Cardiac output apparatus as recited in claim 8 wherein said plateau analysis means is responsive to a signal representing the slope of the input signal in the plateau region.

11. Cardiac output apparatus as recited in claim 8 wherein said plateau analysis apparatus is responsive to a signal representing the width of the plateau region normalized with respect to the patient's heart rate.

12. A method for displaying on a display means the cardiac output of a patient undergoing treatment with an intra-aortic balloon pumping system which icludes an intra-arortic balloon and controller which transmits balloon drive signals for controlling the inflation and deflation of the balloon and arterial pressure signals representing arterial pressure in a patient, the cardiac output display method comprising the steps of:
   A. transmitting a signal representing the arterial pressure excursion of a ventricle ejection pulse in response to the arterial pressure signal, B. transmitting a signal representing the arterial pressure change resulting from balloon deflation in response to the arterial pressure signal,
C. transmitting a signal representing cardiac output in response to the ventricle ejection pulse signal and the balloon deflation signal,
D. energizing the display means with the cardiac output signal.

13. A method for displaying cardiac output as recited in claim 12 additionally comprising the step of monitoring the balloon drive signal, said arterial pressure signal transmitting steps being responsive to the monitored balloon drive signals.

14. A method for displaying cardiac output as recited in claim 12 additionally comprising the step of obtaining a ratio of the ventricle ejection pressure signal and the balloon deflation pressure signal for use in the transmission of the output signal.

15. A method for displaying cardiac output as recited in claim 12 wherein the controller transmits balloon volume signals. said output signal transmitting step including:
i. the step of transmitting the output signal (CO) in accordance with $$CO = (P_2 P_1)(HR)(BV)$$

wherein $P_2$ corresponds to the ventricle ejection pressure, $P_1$ corresponds to the balloon deflation pressure, BV corresponds to the heart rate, and
ii. the step of measuring the heart rate.

16. A method for displaying cardiac output as recited in claim 15 additionally comprising the step of monitoring the balloon drive signal, said arterial pressure signal transmitting step being responsive to the monitored balloon drive signals.

17. A method for displaying cardiac output as recited in claim 16 additionally comprising the steps of
i. transmitting balloon pressure signals representing the pressure in the balloon when the balloon drive signal initiates balloon deflation, and
ii. modifying the cardiac output signals in response to the balloon pressure signals.

18. A method for displaying cardiac output as recited in claim 15 wherein said steps for transmitting the ventricle ejection pulse and balloon deflation pressure signals are operated for each heart beat, said output signal transmitting step including the step of transmitting a final ratio signal based upon the ratio of said signals for each heart beat.

19. A method for displaying cardiac output as recited in claim 15 additionally comprising the steps of
i. analyzing the arterial pressure signal for abnormal conditions, and
ii. indicating the presence of abnormal conditions.

20. A method for displaying cardiac output as recited in claim 15 wherein the arterial pressure signal is characterized by a plateau region in the vicinity of the point of balloon deflation, said method additionally comprising the steps of:
i. analyzing the arterial pressure signal in the plateau region for abnormal conditions, and
ii. indicating the presence of abnormal conditions.

21. A method for displaying cardiac output as recited in claim 20 wherein said analyzing step includes the measurement of the magnitude of the arterial pressure signal in the plateau region.

22. A method for displaying cardiac output as recited in claim 20 wherein said analyzing step includes the measurement of the slope of the arterial pressure signal in the plateau region.

23. A method for displaying cardiac output as recited in claim 20 wherein said analyzing step includes the measurement of the width of the plateau region normalized with respect to the patient's heart rate.

* * * * *

UNITED STATES PATENT AND TRADEMARK OFFICE
CERTIFICATE OF CORRECTION

PATENT NO. : 3,985,123
DATED : October 12, 1976
INVENTOR(S) : George A. Herzlinger, Armando Federico and Arthur R. Kantrowitz It is certified that error appears in the above-identified patent and that said Letters Patent are hereby corrected as shown below:

Column 5, line 26, for "form" read --from--; Column 5, line 31, for "writers" read --writes--; Column 10, line 57, for "FIG. 5A" read --FIG. 7A--; Column 12, line 50, for "monstable" read --monostable--; Column 14, claim 5, line 18, for "CO = $(p_2/P_1)$(HR)(BV)" read --CO = $(P_2/P_1)$(HR)(BV)--; Column 15, claim 15, line 7, for "CO = $(P_2 P_1)$(HR)(BV)" read -- CO = $(P_2/P_1)$(HR)(BV)--; Column 15, line 31, for "pressure, BV corresponds to the heart rate, and" read --pressure, BV corresponds to the balloon volume and HR corresponds to the heart rate, and--; and Column 16, line 9, for "operated" read --operable--.

Signed and Sealed this

Twenty-fifth Day of January 1977

[SEAL]

Attest:

RUTH C. MASON
*Attesting Officer*

C. MARSHALL DANN
*Commissioner of Patents and Trademarks*